131

United States Patent
Das et al.

(10) Patent No.: US 10,188,589 B2
(45) Date of Patent: Jan. 29, 2019

(54) DEPOSITION OF HYDROPHOBIC ACTIVES IN THE PRESENCE OF SURFACTANTS

(71) Applicant: Dow Global Technologies LLC, Midland, MI (US)

(72) Inventors: Debanjan Das, Midland, MI (US); Dale Schmidt, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 480 days.

(21) Appl. No.: 14/766,673

(22) PCT Filed: Jan. 24, 2014

(86) PCT No.: PCT/US2014/012904
§ 371 (c)(1),
(2) Date: Aug. 7, 2015

(87) PCT Pub. No.: WO2014/130204
PCT Pub. Date: Aug. 28, 2014

(65) Prior Publication Data
US 2015/0374594 A1   Dec. 31, 2015

Related U.S. Application Data

(60) Provisional application No. 61/767,407, filed on Feb. 21, 2013.

(51) Int. Cl.
| | | |
|---|---|---|
| *A61K 8/00* | (2006.01) |
| *A61K 8/11* | (2006.01) |
| *A61K 8/41* | (2006.01) |
| *A61Q 13/00* | (2006.01) |
| *A61K 8/73* | (2006.01) |
| *A61K 8/84* | (2006.01) |
| *A61Q 19/10* | (2006.01) |
| *A61K 8/06* | (2006.01) |
| *A61K 8/34* | (2006.01) |
| *A61K 8/35* | (2006.01) |
| *A61K 8/37* | (2006.01) |
| *A61K 8/46* | (2006.01) |
| *A61K 8/49* | (2006.01) |

(52) U.S. Cl.
CPC ............... *A61K 8/11* (2013.01); *A61K 8/06* (2013.01); *A61K 8/34* (2013.01); *A61K 8/35* (2013.01); *A61K 8/37* (2013.01); *A61K 8/416* (2013.01); *A61K 8/463* (2013.01); *A61K 8/4973* (2013.01); *A61K 8/731* (2013.01); *A61K 8/736* (2013.01); *A61K 8/84* (2013.01); *A61Q 13/00* (2013.01); *A61Q 19/10* (2013.01); *A61K 2800/28* (2013.01); *A61K 2800/5426* (2013.01); *A61K 2800/56* (2013.01); *A61K 2800/57* (2013.01)

(58) Field of Classification Search
None
See application file for complete search history.

(56) References Cited

U.S. PATENT DOCUMENTS

| | | | |
|---|---|---|---|
| 3,577,515 A | 5/1971 | Vandegaer | |
| 2003/0211952 A1 | 11/2003 | Erazo-Majewicz et al. | |
| 2010/0086575 A1* | 4/2010 | Dihora | A61K 8/11 424/401 |
| 2012/0104639 A1 | 5/2012 | Traynor et al. | |
| 2013/0122070 A1* | 5/2013 | Barnett | A61K 8/11 424/401 |

FOREIGN PATENT DOCUMENTS

| | | |
|---|---|---|
| CN | 101554573 A | 10/2009 |
| WO | 2008098387 A1 | 8/2008 |

\* cited by examiner

*Primary Examiner* — Necholus Ogden, Jr.
(74) *Attorney, Agent, or Firm* — Thomas S. Deibert

(57) ABSTRACT

Described are personal care compositions, comprising an anionic surfactant, and a polyurea shell encapsulating a hydrophobic active, wherein the polyurea shell has at least one covalently attached cationic polymer, selected from the group consisting of quaternary amines and cationic biopolymers.

10 Claims, No Drawings

DEPOSITION OF HYDROPHOBIC ACTIVES IN THE PRESENCE OF SURFACTANTS

FIELD

The present invention relates to a personal care compositions, and methods for depositing hydrophobic actives.

BACKGROUND

In the personal care field, there is a need for materials which encapsulate or entrain hydrophobic actives. Encapsulation offers known benefits such as compatiblizing the hydrophobic actives with an aqueous systems, and isolating and protecting the hydrophobic actives to preserve their potency.

Theoretically, encapsulation is also intended for delivering hydrophobic actives to a person's skin or hair. One suggestion to accomplish this benefit has been to give the encapsulated hydrophobic active a positive charge in order to better bind to negatively charged surfaces, such as skin or hair. However, this approach has serious drawbacks when used in surfactant-containing personal care products. Many surfactant-containing personal care products contain relatively high levels of anionic components, which compete with the hair or skin for positively charged components, thereby preventing an adequate amount of encapsulated hydrophobic active to be deposited on the hair or skin.

Accordingly, what is needed are new encapsulated hydrophobic active systems which address the above-described needs.

DETAILED DESCRIPTION

In one embodiment, the present invention provides personal care compositions, comprising an anionic surfactant, and a polyurea shell encapsulating a hydrophobic personal care active selected from the group consisting of a fragrance, a vitamin, an extract, or a therapeutic active, wherein the polyurea shell has at least one covalently attached cationic polymer, selected from the group consisting of quaternary amines and cationic biopolymers.

"Personal care" relates to compositions to be topically applied to a person's hair or skin, but not ingested orally.

Preferably, the present compositions are to be topically applied to a person's skin during rinse-off applications. Contemplated are personal care compositions comprising an anionic surfactants which include body-washes, shower gels, exfoliating compositions, shampoos, rinse-off conditioners, shaving foams, face washes, cleansers, hand washes, cleansing creams/milks, astringent lotions, skin toners or fresheners, bubble baths, soluble bath oils, and bar soaps.

In one embodiment, the anionic surfactant is sodium laureth sulfate, ammonium/sodium lauryl sulfate, sodium lauryl sulfoacetate, disodium lauryl sulfosuccinate, sodium methyl 2-sulfolaurate, sodium dodecylbenzene sulfonate, the sodium salt of oleic acid, and the sodium salt of stearic acid. In one embodiment, the anionic surfactant is present in a range from 1 to 25 wt. %. It is understood that, used herein, wt. % means percentage by weight of the personal care ingredients (for example, actives or surfactants) to the final personal care product composition.

A "polyurea shell" refers to the reaction product of polyisocyanates (those for isocyanates with at least 2 reacting groups) and cross-linkers, which, when created via an interfacial condensation reaction between an aqueous phase and an oil phase, results in a polyurea shell encapsulating the oil phase. An example of an interfacial condensation reaction is given by U.S. Pat. No. 3,577,515 which is expressly incorporated by reference herein. Examples of polyisocyanates include toluene diisocyanate (TDI), diisocyanato-diphenylmethane (MDI), derivatives of MDI such as polymethylene polyphenylisocyanate isophorone diisocyanate, 1,4-diisocyanatobutane, phenylene diisocyanate, hexamethylene diisocyanate, 1,3-bis(isocyanatomethyl)benzene, 1,8-disocyanatooctane, 4,4'-methylenebis(phenyl isocyanate), 4,4'-methylenebis(cyclohexyl isocyanate) and mixtures thereof.

The "hydrophobic personal care active" is a personal care performance functional ingredient that is hydrophobic. In most cases, this refers to oils or substances that are soluble in an oil. More specifically, hydrophobic refers to a compound that is more soluble in dodecane than in water. Such components generally have a log octanol/water (partition coefficient) greater than 1.

Examples of fragrances include essential oils, and blends constituting fine fragrances or those typically used in cosmetics or personal care compositions. Determining which compositions are considered a fragrance is well within the technical skill of those skilled in the personal care art. In one embodiment, the preferred hydrophobic personal care active is a fragrance.

Examples of vitamins include all hydrophobic vitamins, such as Vitamin A, Vitamin D, Vitamin E, and Vitamin K. Vitamin E is especially preferred.

"Extracts" include natural hydrophobic botanical or animal extracts. Certain extracts have one or more well known active properties/benefits, for example, skin lightening (turmeric, red clover, horseradish, wild strawberry, mulberry, kojic acid), anti-acne (tea tree, neem, thyme, lavender oil, burdock, olive leaf, dandelion root), anti-aging/anti-wrinkle (garlic, bilberry, ginkgo, ginseng, gotu kola, milk thistle, turmeric, peppermint, epidermal growth factor (rh-oligopeptide-1, EGF), coffee arabica extract), moisturizing (aloe vera, jojoba oil, cocoa butter, avocado oil, spermaceti, lanolin, lecithin, beeswax), anti-inflammatory (ginger, boswellin, willow bark, arnica, cayenne pepper, omega 3 fish oil, flaxseed oil), skin toning (chamomile, elder, lavender, parsley, sage, rose hips, yarrow), anti-microbial (garlic, tea tree, thyme, rosemary, goldenseal, elderberry, barberry, grape), anti-itch (aloe-vera, calendula, witch hazel, St. John's wort, mullein, chamomile, neem, oats, wild pansy), anti dandruff (neem, black pepper, sandalwood, ginger, tea tree, burdock), immunosuppressant (turmeric, triptolide, licorice, berbamine, tanacetum, astragalus), or insect repellent (citronella oil, pennyroyal, lavender, rose geranium).

There are also synthetic hydrophobic compounds which have one or more well known active properties/benefits, and are deemed "therapeutic actives" herein for convenience of nomenclature to distinguish from the above extracts. Examples of therapeutic actives include those with benefits such as skin lightening (hydroquinone, tretinoin, glutathione), anti-acne (salicylic acid, benzoyl peroxide, tretinoin, adapalene, azelaic acid, tazarotene), anti-aging/anti-wrinkle (idebenone, 1-selenomethionine (selenium), alpha lipoic acid, polyphenols, retinoids), moisturizing (cetyl alcohol, glyceryl stearate, stearyl alcohol, mineral oil, petrolatum), anti-inflammatory (ibuprofen, celecoxib, diclofenac, phenyl butazone, desonide, betamethasone), anti-microbial (clindamycin, ketoconazole, mupirocin, erythromycin), anti-itch (corticosteroids, menthol), antidandruff (zinc pyrithione, selenium sulfide, coal tar, ketoconazole), immunosuppressant (azathioprine, methotrexate), or sunscreens (octyl methoxycinnamate, avobenzone, para aminobenzoic acid, homosalate, titanium dioxide, zinc oxide, benzophenones, benzylidenes, salicylates, or other known hydrophobic UV filters).

As can be readily appreciated, the above-listed extracts and therapeutic actives could be combined to support the same benefit (in common), or used together in a combination of disparate benefits.

In one embodiment, the hydrophobic personal care active is present in a range from 0.1 to 10 wt. %.

It is understood that the polyurea shell must have at least one covalently attached cationic polymer. This is readily distinguished from situations where the cationic polymer is added after the formation of the polyurea shell, because in such cases, the cationic polymer will not graft to the polyurea shell after the fact in the presence of anionic surfactant (see Example 3 below). Upon information and belief, the polyurea shell is not reactive due to cross-linking, but even were this not the case, the anionic surfactant will more effectively compete for the cationic polymer and the cationic polymer will be desorbed from the surface of the capsule by the anionic surfactant thereby rendering the loss of functionality of the cationic polymer.

In one embodiment, the polyurea shell has at least two covalently attached cationic polymers.

"Quaternary amine" refers conventionally to a compound formed from at least one amine (or its salt) bearing four substituents, resulting in a permanent positive charge. Preferably, one of the substituents should be further substituted with a primary amino group or a secondary amino group. Such a preferred quaternary amine compound is (2-Aminoethyl) trimethylammonium chloride. It should be understood that when the present application refers to covalently attached quaternary amine, it refers to the reaction product of a quaternary amine compound and polyisocyanate, the quaternary amino group itself does not react, but rather one of the substituents of the amine compound covalently attaches to the polyurea shell, leaving the quaternary amino group tethered to the polyurea shell by said substituent. In one embodiment, the quaternary amine is present in a range from 0.001 to 0.2 wt. %.

"Cationic biopolymer" refers to naturally occurring positively charged biopolymers, such as hylauronic acid and chitosan. Preferably, the cationic biopolymer is chitosan. Most preferably, the chitosan is KYTAMER™ PC (INCI: chitosan PCA) derivative, available from The Dow Chemical Company (Midland, Mich.). In one embodiment, the cationic biopolymer is present in a range from 0.001 to 0.1 wt. %.

In one embodiment, wherein the polyurea shell has at least one covalently attached quaternary amine and at least one covalently attached cationic biopolymer.

In another embodiment, the present invention provides a method of depositing fragrance of an individual's skin, comprising encapsulating the fragrance in a polyurea shell, wherein the polyurea shell has at least one covalently attached cationic polymer, selected from the group consisting of quaternary amines and cationic biopolymers, incorporating the polyurea shell into a body wash, and applying the body wash to the individual. It is expressly contemplated that the bodywash contains at least one anionic surfactant.

In one embodiment, the step of encapsulating includes emulsifying an oil phase containing the fragrance and an aqueous phase containing the cationic polymer, provided that the emulsion is formed before the polyurea shell. Preferably, the polyurea shell has at least one covalently attached quaternary amine and at least one covalently attached cationic biopolymer. The polyurea shell, it is understood, is formed by crosslinking a polyisocyanate, preferably isophorone diisocyanate. In some embodiments, an ultra-hydrophobe, such as cottonseed oil, is added to the oil phase. In these cases, the cottonseed oil is present in a range from 0.1 to 5 wt. %.

EXAMPLES

Example 1

A stock fragrance blend comprising of five individual fragrance components was created with the individual fragrances chosen to represent a wide spectrum of hydrophobicity and vapor pressure, listed in Table 1 in wt %.

TABLE 1

|  | Blend 1 |
|---|---|
| Dihydromyrcenol | 20 |
| Butylcylohexyl acetate | 20 |
| Verdyl acetate | 10 |
| Octahydro tetramethyl acetonaphtone | 30 |
| Oxacycloheptadec-8-en-2-one | 20 |

To Blend 1 is added a fluorescent lipophilic dye [DiO, D275 3,3'-dioctadecyloxa-carbocyanine perchlorate in ethanol solution] at an effective concentration of 0.001%, to quantify deposition, as will be explained in Example 4.

An exemplary body wash is represented by commercially available, STEOL CS-270 (Stepan Co., Northfield, Ill.) containing 70% Sodium Laureth Sulfate (SLES), diluted with DI water to get a final concentration of 12.064% of SLES in water, with pH 7.

Example 2

Fragrance encapsulated according to the present invention is shown in Table 2, with components listed in wt. %.

TABLE 2

|  | Batch 1 | Batch 2 | Batch 3 |
|---|---|---|---|
| Fragrance Mixture (Example 1) | 20.3 | 20.3 | 20.3 |
| Isophorone Diisocycante (IPDI) | 2.28 | 2.28 | 2.28 |
| Cottonseed oil | 0.20 | 0.20 | 0.20 |
| Lipophilic Dye DiO, D275 | 0.0002 | 0.0002 | 0.0002 |
| Brij 35:58 (1:1) | 1.37 | 1.37 | 1.37 |
| Water | 75.3 | 68.4 | 68.3 |
| (2-Aminoethyl) trimethylammonium chloride (AEAC) | 0.14 | — | 0.14 |
| KYTAMER chitosan PCA derivative | — | 0.033 | 0.033 |
| Tetraethylene Pentamine (TEPA) | 0.23 | 0.23 | 0.23 |
| Ethylene Diamine (EDA) | 0.18 | 0.18 | 0.18 |

To synthesize representative polyurea shells, the oil phase (fragrance mixture, cottonseed oil, fluorescent dye and IPDI) was combined and mixed until uniform. The aqueous phase containing surfactant Brij 35:58 stock solution, water, and chitosan derivative (when present), and/or AEAC (when present), are added to the mixture and mixed with an IKA Ultra Turrax T25 at 8000 rpm for about 60 seconds to create an emulsion.

Crosslinkers EDA and TEPA were added to all formulations to react with the IPDI to create a shell that surrounds, or encapsulates, the oil phase.

Example 3

Comparative

Fragrance encapsulated according to conventional methods is shown in Table 3, with components listed in wt. %.

TABLE 3

|  | Comparative Batch A | Comparative Batch B |
|---|---|---|
| Fragrance Mixture (Example 1) | 20.3 | 20.3 |
| Isophorone Diisocycante (IPDI) | 2.28 | 2.28 |
| Cottonseed oil | 0.20 | 0.20 |
| Lipophilic Dye DiO, D275 | 0.0002 | 0.0002 |
| Brij 35:58 (1:1) | 1.37 | 1.37 |
| Water | 75.4 | 75.4 |
| Cationic surfactant ARQUAD 18-50 (1-octadecanaminium, n,n,n-trimethyl chloride) | 0.050 | 0.00 |
| Cationic polymer SOFTCAT Sx-400H (Polyquaternium-67) | 0.00 | 0.046 |
| Tetraethylene Pentamine (TEPA) | 0.23 | 0.23 |
| Ethylene Diamine (EDA) | 0.18 | 0.18 |

Polyurea capsules were synthesized according to the method of Example 2, except that the cationic surfactant or cationic polysaccharide is added after the cross-linker. Upon information and belief, the cationic surfactant or cationic polysaccharide, is not covalently linked to the polyurea shell.

Example 4

Encapsulated compositions substantially according to Examples 2 and 3 were prepared, and added to a representative body wash made from commercially available STEOL CS-270 surfactant blend (Stepan Co., Northfield, Ill.) containing 70% Sodium Laureth Sulfate (SLES), diluted with DI water to get a final concentration of 12.064% of SLES in water, with pH 7. Accordingly, the fragrance-loaded capsules were incorporated into the body wash base at an equivalent concentration of 2% of free fragrance.

To test bioadhesion (skin deposition), about 4 g of the above described body washes were applied on hairless Yucatan pig skin of constant area (approximately 0.5"×0.5") with intact stratum corneum for 2 minutes and rinsed off with de-ionized water at room temperature for 4 minutes.

Bioadhesion was also measured by deposition to glass slides thoroughly cleaned with soap and DI water. Body wash with incorporated polyurea shells equivalent to free fragrance concentration of 2% was applied on the glass slides for 2 minutes, then rinsed-off with DI water for 4 minutes with a rocking action. The slides were measured for residual fluorescent signals. The residual fluorescence after rinse-off was measured with fluorescence imaging with excitation at 484 nm & emission at 501 nm. Because the lipophilic fluorescent dye was encapsulated along with the fragrance, the residual fluorescence seen is directly proportional to bioadhesion of frangrance-containing polyurea shells.

Results of encapsulated fragrance deposited on the glass substrate (which followed the trends noted in skin) is shown in Table 4, in a ratio of pixel intensity corresponding to residual fluorescence, which is directly proportional to bioadhesion of the encapsulated fragrance:

TABLE 4

|  | Relative Bioadhesion |
|---|---|
| Un-encapsulated Fragrance | 1.0 |
| Batch 1 | 2.9 |
| Batch 2 | 4.4 |
| Batch 3 | 6.4 |
| Comparative Batch A | 1.0 |
| Comparative Batch B | 1.0 |

Batch 3 shows a synergistic 6.41 times increase in bioadhesion when compared to Batches 1 and 2. All three inventive samples demonstrate that encapsulated fragrances can achieve bioadhesion in body wash bases, which are loaded with anionic surfactants. Without being bound by theory, covalently cationically modified polyurea shells significantly outperformed Comparative Batches A and B, polyurea shells that were merely associated with conventional cationic additives, which were added physically after the shell formation and are not chemically attached to the shell surface.

The invention claimed is:

1. A personal care composition, comprising:
   an anionic surfactant; and
   a polyurea shell encapsulating a hydrophobic personal care active selected from the group consisting of a fragrance, a vitamin, an extract, or a therapeutic active, wherein the polyurea shell has at least one covalently attached cationic polymer, selected from the group consisting of quaternary amines and cationic biopolymers, wherein the polyurea shell has at least one covalently attached quaternary amine that is the reaction product of (2-Aminoethyl) trimethylammonium chloride and polyisocyanate.

2. The personal care composition of claim 1, wherein the polyurea shell has at least two covalently attached cationic polymers.

3. The personal care composition of claim 1, wherein the polyurea shell has at least one covalently attached quaternary amine and at least one covalently attached cationic biopolymer.

4. The personal care composition of claim 1, wherein the hydrophobic personal care active is present in a range from 0.1 to 10 wt. %.

5. The personal care composition of claim 1, wherein the hydrophobic personal care active is a fragrance.

6. The personal care composition of claim 1, wherein the quaternary amine is present in a range from 0.001 to 0.2 wt. %.

7. The personal care composition of claim 1, wherein the cationic biopolymer is chitosan.

8. The personal care composition of claim 1, wherein the cationic biopolymer is present in a range from 0.001 to 0.1 wt. %.

9. The personal care composition of claim 1, wherein the anionic surfactant is sodium laureth sulfate, ammonium/sodium lauryl sulfate, sodium lauryl sulfoacetate, disodium lauryl sulfosuccinate, or sodium methyl 2-sulfolaurate.

10. The personal care composition of claim 1, wherein the anionic surfactant is present in a range from 1 to 25 wt. %.

* * * * *